United States Patent [19]
Colleran et al.

[11] Patent Number: 5,609,643
[45] Date of Patent: Mar. 11, 1997

[54] KNEE JOINT PROSTHESIS

[75] Inventors: Dennis P. Colleran, Plainville; Robert E. Sommerich; Jorge A. Ochoa, both of Norton, all of Mass.

[73] Assignee: Johnson & Johnson Professional, Inc., Raynham, Mass.

[21] Appl. No.: 404,195

[22] Filed: Mar. 13, 1995

[51] Int. Cl.$^6$ ................................................ A61F 2/38
[52] U.S. Cl. .................................................... 623/20
[58] Field of Search .................................. 623/16, 18, 20

[56] References Cited

U.S. PATENT DOCUMENTS

| | | |
|---|---|---|
| 4,714,472 | 12/1987 | Averill et al. . |
| 5,007,933 | 4/1991 | Sidebotham et al. . |
| 5,171,276 | 12/1992 | Caspari et al. . |
| 5,197,987 | 3/1993 | Koch et al. ............................ 623/20 |
| 5,201,768 | 4/1993 | Caspari et al. . |
| 5,236,461 | 8/1993 | Forte ...................................... 623/20 |
| 5,326,361 | 7/1994 | Hollister ................................. 623/20 |
| 5,330,534 | 7/1994 | Herrington et al. .................... 623/20 |
| 5,370,699 | 12/1994 | Hood et al. . |
| 5,387,240 | 2/1995 | Pottenger et al. ...................... 623/20 |

*Primary Examiner*—David Isabella
*Attorney, Agent, or Firm*—William C. Geary, III; Nutter, McClennen & Fish, LLP

[57] ABSTRACT

A knee joint prosthesis includes a femoral component, a tibial plateau and a tibial bearing member. The design and geometry of the articulation surfaces of the condylar elements of the femoral component and tibial bearing member is such that contact area between the articulation surfaces is maximized both in perfect alignment and in malalignment conditions. Moreover, contact stresses placed upon the articulation surfaces in perfect alignment and in malalignment are reduced. High contact area and low contact stress on the articulation surfaces can be maintained even while matching knee prosthesis components of different sizes.

11 Claims, 10 Drawing Sheets

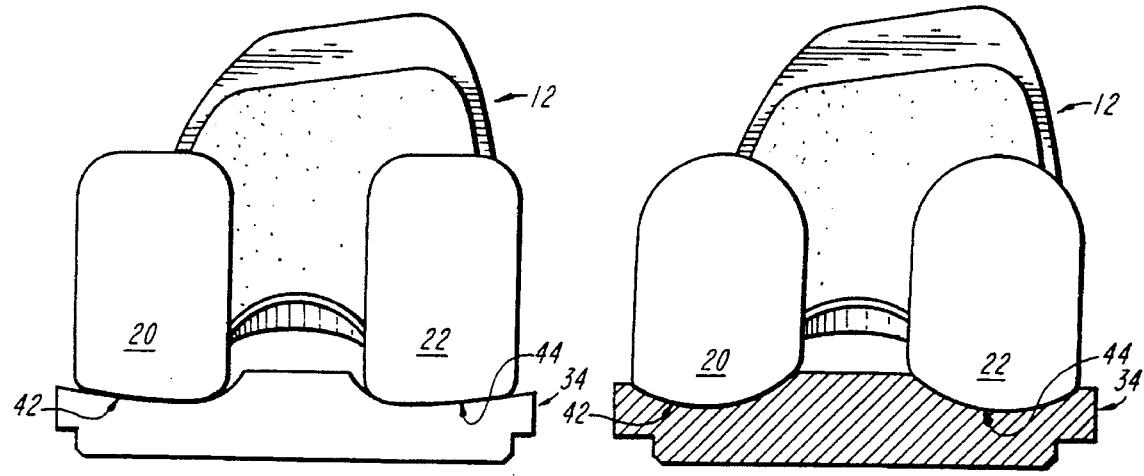
*FIG. 6A*  *FIG. 6B*
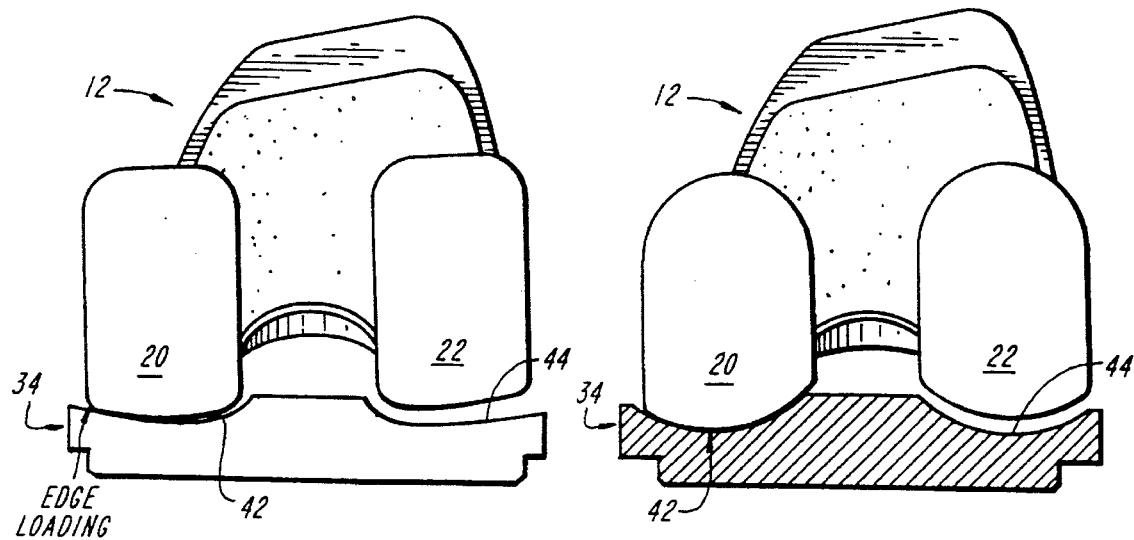
*FIG. 7A*  *FIG. 7B*

KNEE JOINT PROSTHESIS

BACKGROUND OF THE INVENTION

The invention relates to implantable bone prostheses, and more particularly to knee joint prostheses.

Joint replacement surgery is quite common and enables many individuals to function normally when otherwise it would not be possible to do so. Artificial joints are normally composed of metallic and/or ceramic components that are fixed to existing bone.

Knee arthroplasty is a well known surgical procedure by which a diseased and/or damaged natural knee joint is replaced with a prosthetic knee joint. Typical knee prostheses include a femoral component, a patella component, a tibial tray or plateau, and a tibial bearing member. The femoral component generally includes a pair of laterally spaced apart condylar portions, the inferior or distal surfaces of which articulate with complementary condylar elements formed in a tibial bearing component.

In a properly functioning artificial knee joint, the condylar portions of the femoral component must slide and roll freely over the articulation surface formed by the condylar elements of the tibial bearing member. Natural friction within a replaced, artificial joint can lead to the development of wear debris in which minute particles of debris (e.g., metal or plastic from the prosthesis) become dislodged and migrate within the joint. The phenomenon of wear debris within artificial joints is a serious problem thin can inhibit the proper mechanical functioning of the joint. Moreover, wear debris can lead to osteolysis and bone deterioration. When wear debris develops within an artificial joint, surgical removal of the debris or subsequent replacement of the artificial joint is often necessary.

During normal usage of a properly implanted prosthetic knee joint, load and stress are placed on the tibial bearing member. The tibial bearing member is typically made of an ultrahigh molecular weight polyethylene (UHMWPE), and friction, continuous cycling and stress can cause some erosion and/or fracture of the tibial bearing member, thus leading to wear debris. The risk of wear debris can be even greater during malalignment of an artificial knee joint, which can result from normal usage or from imperfect and/or inaccurate implantation of the prosthesis within a patient. During malalignment the load upon the tibial bearing member is not evenly distributed. Instead, excess load is placed on certain areas of the tibial bearing member. This uneven distribution of load (or edge loading) can accelerate the development of wear debris. Contact stresses on the tibial bearing member increase substantially with malalignment of the joint, thus increasing the risk that wear debris will develop when a prosthetic knee joint is subjected to malalignment conditions.

Joint replacement surgery obviously requires a tremendous degree of precision to ensure that prosthetic components are properly sized, implanted, and aligned. Imperfect sizing, implantation and alignment can lead to inadequate performance of the knee joint as well as to the presence of high contact stresses in certain areas of the prosthesis, thus leading to the possible development of wear debris.

The anatomy of patients who undergo knee arthroplasty is widely variable and can lead to difficulty in matching the standard sized prosthetic components that form a prosthetic joint. Many prosthetic components are manufactured such that similarly sized components must be used together and implanted within a patient when replacing a natural joint. That is, the femoral component, tibial bearing member, and tibial plateau that form the artificial knee joint must normally be of a matched size. If the components are not size-matched, inappropriate edge loading may develop and accelerate wear.

There is thus a need for knee joint prostheses that have a reduced tendency to develop wear debris due to the maintenance of good contact area and low contact stress between femoral and tibial components, even during the dynamics of daily activity and in various conditions of malalignment, with the options of matched or mismatched condylar sizes.

Accordingly, it is an object of the present invention to provide knee joint prostheses with improved performance and a longer useful life. It is also an object of the invention to provide knee joint prostheses having a reduced tendency to develop wear debris. A further object of the invention is to provide knee joint prostheses which are able to maintain good contact area and low contact stress between femoral and tibial components throughout normal usage conditions and in conditions of malalignment. Another object of the invention is to provide knee joint prostheses that enable the mixing of component sizes while still maintaining low contact stresses between femoral and tibial components. These and other objects will be apparent from the description that follows.

SUMMARY OF THE INVENTION

The invention provides a knee joint prosthesis in which the articulation surfaces of the femoral and tibial components are configured to maintain good contact area and low contact stress when implanted in a patient. The femoral component of the knee joint prosthesis has a proximal surface which is mountable on a distal end of the femur of a patient, and a distal articulation surface that includes two adjacent, semi-parallel bearing surfaces that form femoral condyles. Each femoral condyle is of a curved, convex shape in both the anterior-posterior direction and in the medial-lateral direction. The curvature of each femoral condyle lying in the sagittal plane, in contact with a tibial condylar element, and extending in the anterior-posterior direction is defined by at least two semi-parallel radii wherein a first sagittal radius is more anterior than a second sagittal radius with the first and second sagittal radii being offset from one another by the distance between their respective centers of curvature. Preferably, the centers of curvature of the first and second sagittal radii are colinear. The curvature of each femoral condyle lying in the coronal plane, in contact with a tibial condylar element, and extending in the medial-lateral direction is defined by a coronal radius.

The prosthesis also includes a tibial tray or plateau having a proximal end and a distal end that is mountable on the tibia of the patient. Further, the prosthesis includes a tibial bearing member having a distal surface mountable within the proximal end of the tibial plateau component and a proximal articulation surface. The proximal articulation surface of the tibial bearing member includes two adjacent tibial condylar elements that seat the adjacent, semi-parallel bearing surfaces of the femoral component. Each condylar element of the tibial bearing member is of a curved, concave shape in both the anterior-posterior and medial-lateral directions.

The prosthesis of the present invention is characterized by improved contact between the femoral condyles and the tibial condylar elements. Preferably, contact stress between the femoral bearing surfaces and the condylar elements, when subjected to a load of approximately 2060 N, does not exceed approximately 15 MPa when the prosthesis is in perfect alignment and do not exceed approximately 20 MPa when the prosthesis is subjected to varus-valgus lift and internal-external rotation conditions of malalignment. Further, the contact area between the condyles of the femoral component and the condylar elements of the tibial bearing member, when the prosthesis is subjected to approximately 15° flexion, without malalignment, is greater than 200 mm². The contact area between the condyles of the femoral component and the condylar elements of the tibial bearing member, when the prosthesis is subjected to approximately to 15° flexion and 3° varus-valgus lift, is greater than 130 mm².

Preferably, the first and second sagittal radii increase with increasing size of the femoral component of the prosthesis while the coronal radius remains substantially constant with increasing sizes of the femoral component. The first sagittal radius is in the range of about 1.020 to 1.885 inches while the second sagittal radius is in the range of about 0.6 to 1.2 inches. The coronal radius preferably is in the range of about 0.7 to 1.1 inches.

The curvature of the tibial condylar elements, in the anterior-posterior direction, is defined by a radius that is approximately 104% to 120% of the first sagittal radius of the bearing surfaces of the femoral component. The curvature of the tibial condylar elements, in the medial-lateral direction, is defined by a radius that is approximately 120% to 152% of the coronal radius of the bearing surfaces of the femoral component.

BRIEF DESCRIPTION OF THE DRAWINGS

FIG. 6A is a posterior view of a prior art femoral component mounted adjacent a prior art tibial bearing member in perfect alignment.

FIG. 6B is a posterior view of the femoral component of the present invention mounted adjacent the tibial bearing member of the present invention in perfect alignment.

FIG. 7A is a posterior view of a prior art femoral component mounted adjacent a prior art tibial bearing member in a malalignment condition having approximately 3° varus-valgus lift.

FIG. 7B is a posterior view of a femoral component of the present invention mounted adjacent a tibial bearing member of the present invention in a malalignment condition having 3° varus-valgus lift.

DETAILED DESCRIPTION OF THE INVENTION

The present invention provides an improved construction for a knee joint prosthesis. The design and the geometry of the knee joint prosthesis of the invention facilitates greater contact between the femoral and tibial components of the knee joint prosthesis. This improved contact increases contact area and reduces contact stress between the articulation surfaces of the artificial joint and accordingly helps to eliminate or greatly reduce the tendency for wear debris to develop within a replaced joint.

Figure 1:
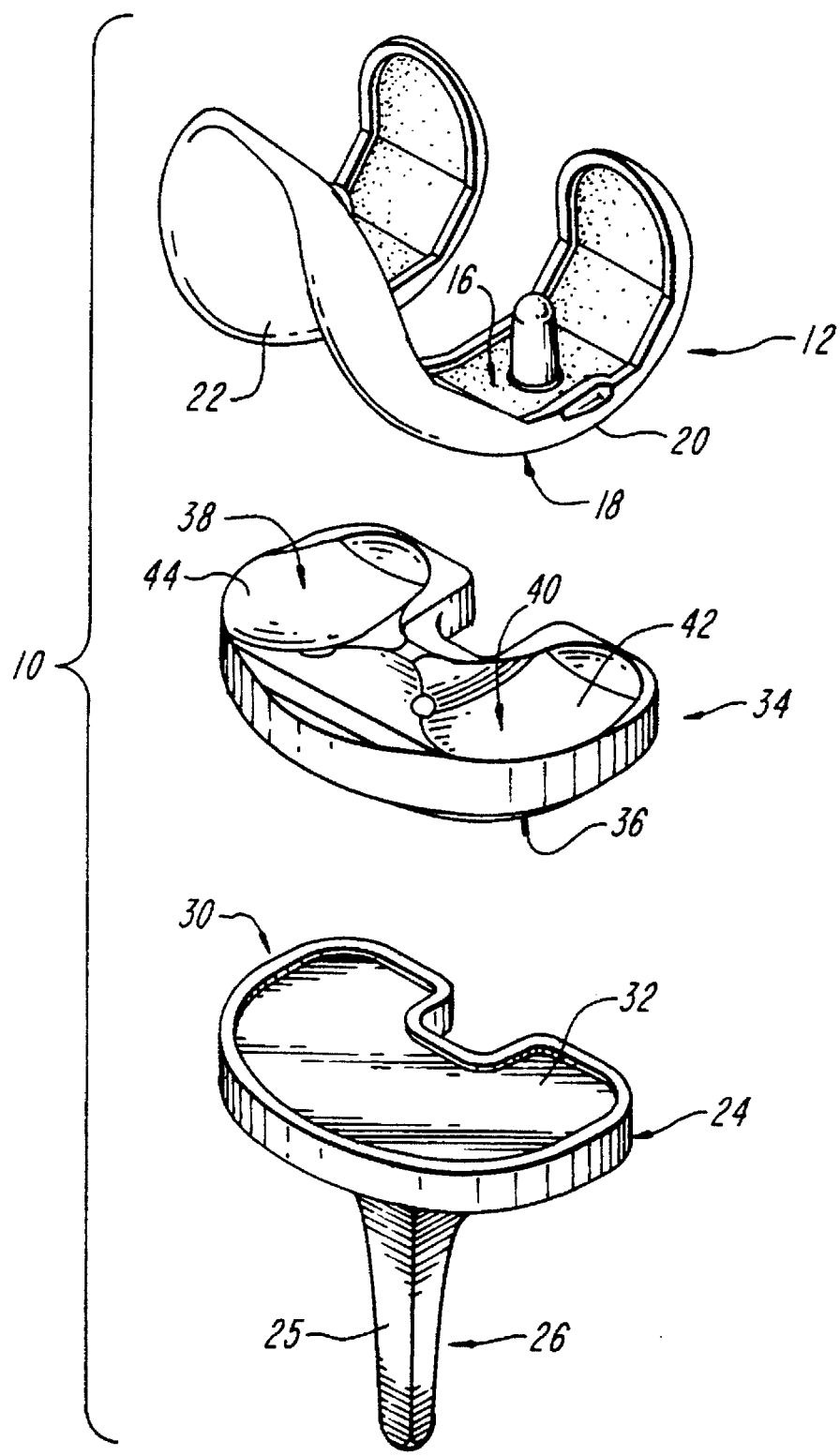
FIG. 1 is an exploded, perspective view of an artificial knee joint illustrating the femoral component, tibial plateau and the tibial bearing member.

FIG. 1 illustrates three components found in a knee joint prosthesis 10 constructed according to the present invention. A femoral component 12 includes an inferior surface 16 which is mountable within the distal end of a patient's femur and a superior articulation surface 18. The articulation surface 18 includes adjacent lateral 20 and medial 22 condyles. The knee prosthesis 10 also includes a tibial tray or plateau 24, the distal end 26 of which includes a distally extending stem 25 which is mountable within the tibia of a patient. The proximal end 30 of the tibial plateau includes a recessed region 32 within which a tibial bearing member 34 is mounted in a mechanical fit.

Figure 2:
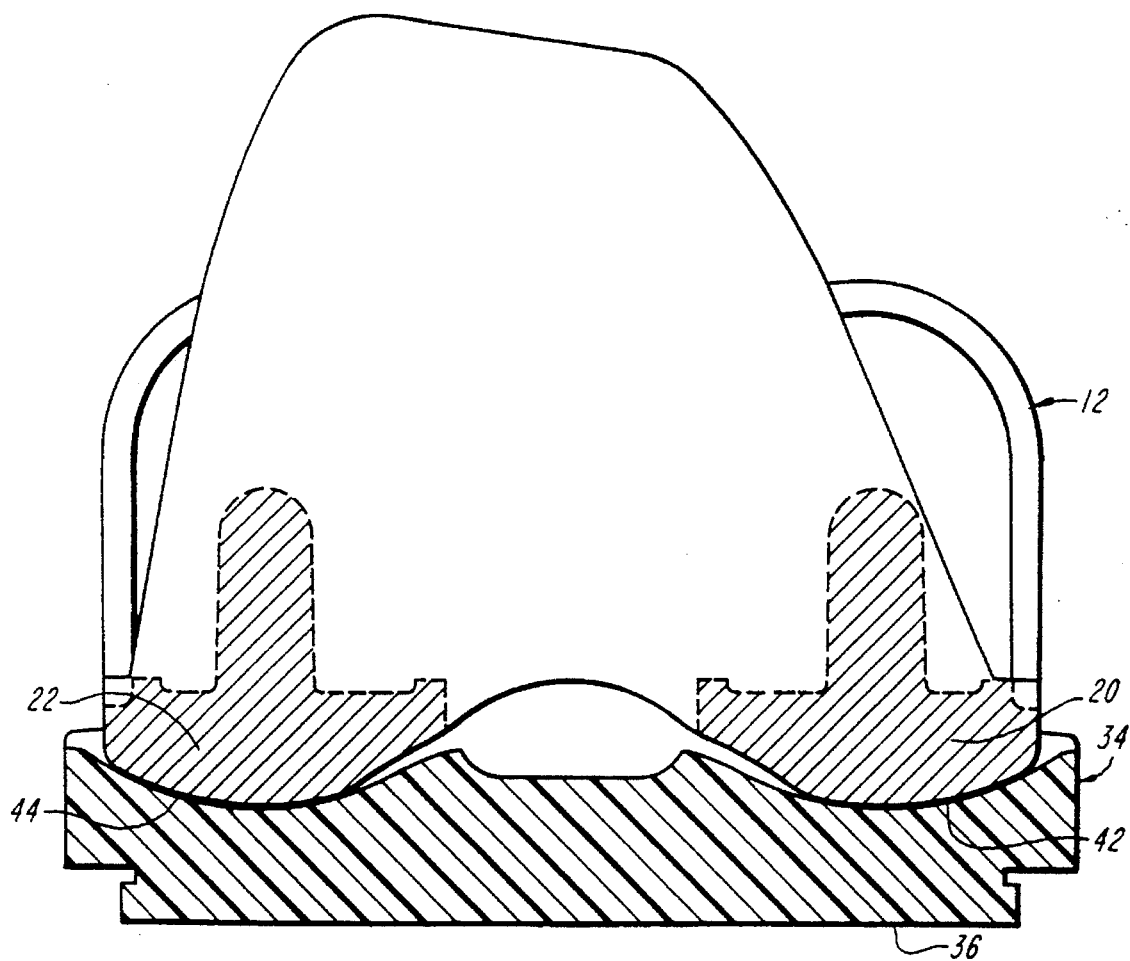
FIG. 2 is an anterior view of an artificial knee femoral component positioned adjacent a prosthetic tibial bearing member, in a condition of perfect alignment.
Figure 3:
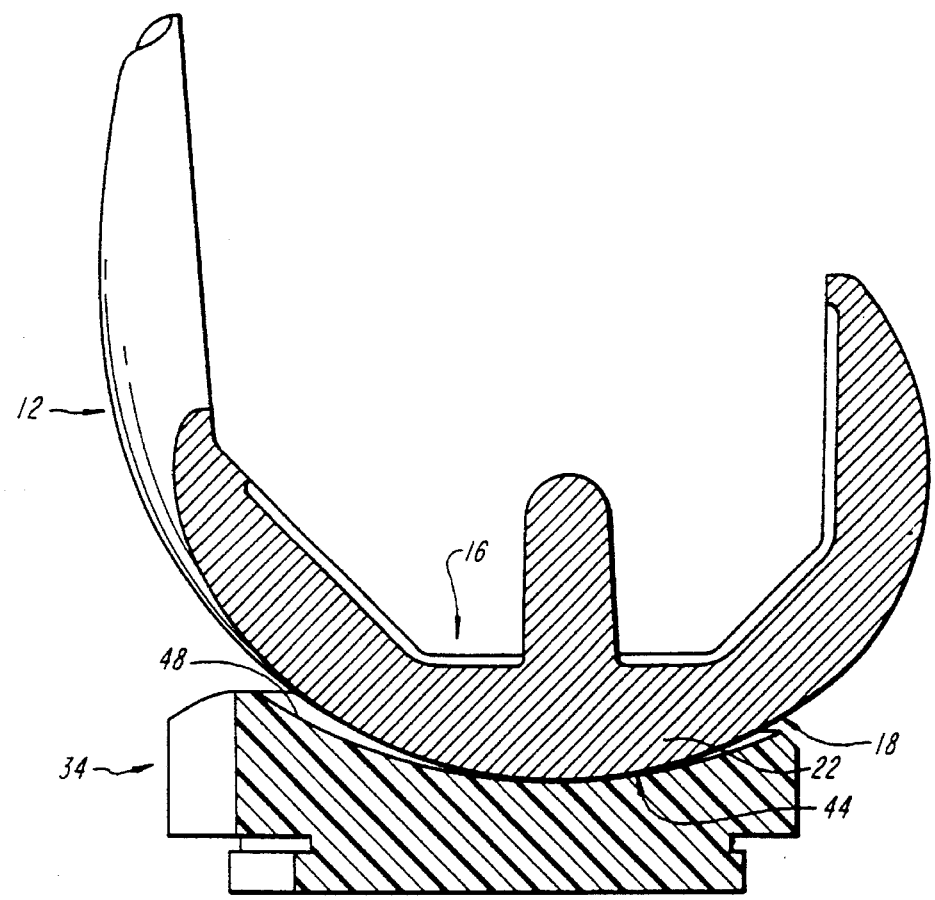
FIG. 3 is a side view from the medial side of an artificial knee femoral component positioned adjacent a prosthetic tibial bearing member, in perfect alignment.
Figure 4:
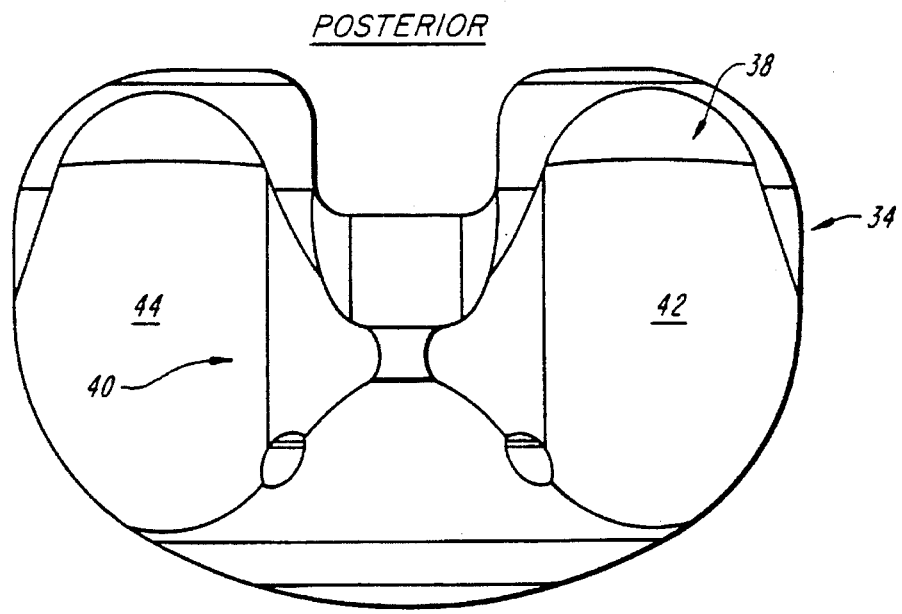
FIG. 4 is a top view of the prosthetic tibial bearing member shown in FIG. 1.

Tibial bearing member 34 includes a distal surface 36 mountable within a recessed region 32 of proximal end 30 of tibial plateau 24. The proximal surface 38 of tibial bearing member 34 forms an articulation surface 40 that engages and articulates with the articulation surface 18 of femoral component 12. The articulation surface 40 of the tibial bearing member 34 includes adjacent lateral 42 and medial 44 condyles. As shown in FIG. 2, the lateral and medial condyles 20, 22 of the femoral component 12 mount in engagement with the lateral and medial condyles 42, 44 of tibial bearing member 34.

Although not illustrated, it is understood that a tibial component of an artificial knee joint can be formed as a single piece which includes portions that correspond to tibial tray component 24 and tibial bearing member 34. Typically, such single piece units are manufactured of ultrahigh molecular weight polyethylene.

The condyles 20, 22 of femoral component 12 and the condyles 42, 44 of tibial bearing member 34 are configured such that when the condyles of these two components engage each other the contact area between the condyles of the femoral component and the condyles of the tibial bearing member is maximized. Greatest contact area is achieved in conditions of perfect alignment, throughout the range of motion of the knee joint, and in conditions of malalignment, including varus-valgus lift and internal-external rotation. The term "perfect alignment", as used herein refers to a condition where the knee joint is subjected to 0° varus-valgus lift, and 0° internal-external rotation throughout the anatomic range of flexion-extension (i.e., about −10° to 135°).

The ability to achieve a large contact area between the condyles of the femoral component and the tibial bearing member is significant because contact stress on the prosthesis components, particularly the tibial bearing member, is minimized. In many instances, the tibial bearing members are manufactured of polymeric materials, such as ultra-high molecular weight polyethylene (UHMWPE). Where loads are unevenly distributed or concentrated across the tibial bearing member during use of an artificial knee joint, edge loading can develop. Edge loading leads to the development of higher contact stresses in certain parts of the prosthesis which, in turn, can cause wear debris to develop within the joint.

FIGS. 2, 3, 5A, 5B and 11 illustrate the femoral component 12 of the present invention, including condyles 20, 22. Each condyle 20, 22 is generally ellipsoid in shape and is of a curved, convex shape in both the anterior-posterior direction and the medial-lateral direction. The curvature of the articulation surface 23 of each condyle 20, 22 lying in the sagittal plane, in contact with the condyles 42, 44 of the tibial bearing member, and extending in the anterior-posterior direction is defined by at least two semi-parallel radii wherein a first sagittal radius is more anterior than a second sagittal radius. The first, more anterior sagittal radius ($R_1$) is offset from the second sagittal radius ($R_2$) by the distance between their respective centers of curvature ($C_1$, $C_2$).

Figure 5A:
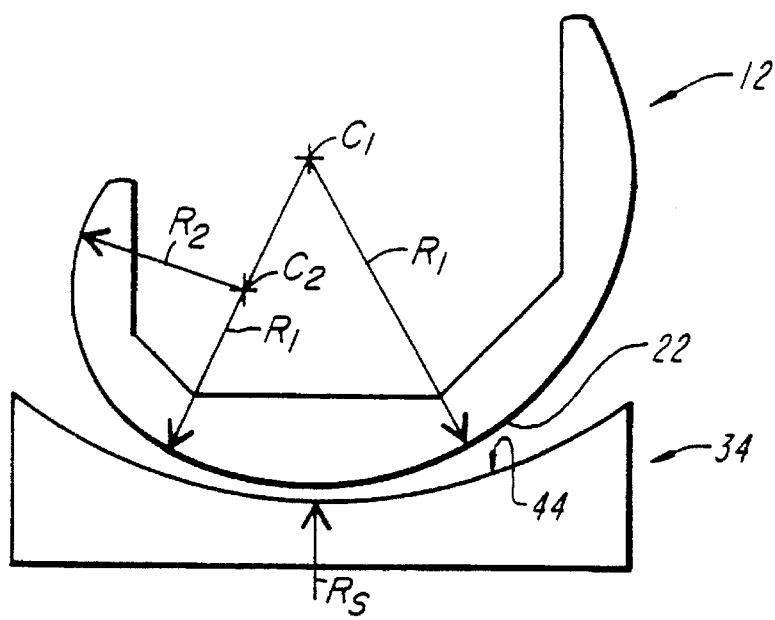
FIG. 5A is a sectional view, in the sagittal plane, of a femoral component and tibial bearing member constructed according to the present invention.

As shown in FIG. 5A, the curvature of the articulation surface 23 lying in the sagittal plane for each condyle 20, 22 can be defined by approximately four radii. However, the critical surface geometry is that which relates to the portion of the condyles 20, 22 which contact the condyles 42, 44 of the tibial bearing member 34. A first sagittal radius ($R_1$) covers an intermediate portion of the articulation surface 23 of each condyle 20, 22 in the sagittal plane along the anterior-posterior direction. Typically, the articulation surface 23 of condyles 20, 22 defined by $R_1$ contacts the articulation surface 40 of tibial bearing member 34 during flexion of the knee between approximately 0° and 40°. The first sagittal radius ($R_1$) is in the range of approximately 1.020 to 1.885 inches.

The second sagittal radius ($R_2$) covers a more posterior portion of the articulation surface 23 of condyles 20, 22 lying in the sagittal plane and extending in the anterior-posterior direction. The articulation surface 23 of condyles 20, 22 defined by $R_2$ typically contacts the articulation surface 40 of tibial bearing member 34 during flexion of the knee greater than about 40°. The second sagittal radius ($R_2$) preferably has a value of approximately 0.6 to 1.2 inches, and more preferably, due to anatomic constraints, of about 0.7 to 1.1 inches.

As illustrated in FIG. 5A, the first and second sagittal radii ($R_1$, $R_2$) originate from their respective centers of curvature ($C_1$, $C_2$). The centers of curvature $C_1$ and $C_2$ are collinear and the center of curvature for $R_2$ ($C_2$) is more posterior than the center of curvature for $R_1$ ($C_1$).

The values of first and second sagittal radii ($R_1$, $R_2$) are, to some extent, dependent upon the size of the femoral component. Typically, femoral components are available in different sizes to accommodate the anatomies of different patients. Femoral components can have dimensions in which the largest width (in the anterior-posterior dimension) ranges from about 50 to 74 mm, and in which the largest width (in the medial-lateral dimension) ranges from about 54 to 78 mm. Table 1 illustrates approximate values for the first and second sagittal radii with varying femoral component sizes.

TABLE 1

| Femoral Component Size | A–P Width (mm) | M–L Width (mm) | $R_1$ Value (inches) | $R_2$ Value (inches) |
|---|---|---|---|---|
| 2 | 56 | 60 | 1.194 | 0.743 |
| 3 | 61 | 66 | 1.321 | 0.794 |
| 4 | 65 | 71 | 1.405 | 0.828 |
| 5 | 69 | 73 | 1.511 | 0.860 |
| 6 | 74 | 78 | 1.750 | 0.950 |

Figure 5B:
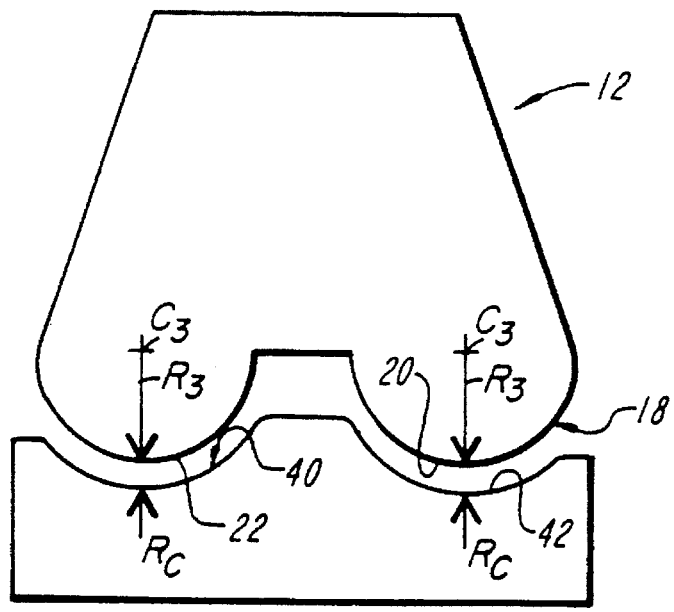
FIG. 5B is a partial sectional view, in the coronal plane, of a femoral component and tibial bearing member constructed according to the present invention.

FIG. 5B illustrates the curvature of articulation surface 23 of condyles 20, 22 lying in the coronal plane and extending in the medial-lateral direction. The curvature of this surface is defined by the coronal radius ($R_3$). Preferably, the coronal radius is in the range of about 0.7 to 1.1 inches. The value of the coronal radius is substantially constant, and is not dependent on the size of the femoral component of the prosthesis. Thus, substantially the same coronal radius can be used without regard to the size of femoral component or tibial bearing member used.

Referring to FIGS. 1 through 4, 10A and 10B, tibial bearing member 34 includes adjacent lateral 42 and medial 44 tibial condylar elements that are generally ellipsoid and are configured to seat on and articulate with condyles 20, 22 of femoral component 12. The tibial condylar elements 42, 44 preferably are of a curved, concave shape. The articulation surface 46 of tibial condylar elements 42, 44 is characterized by a curved, concave surface in both the medial-lateral and anterior-posterior directions. The curvature of the tibial condylar elements 42, 44 lying in the sagittal plane and extending in the anterior-posterior direction is defined by a sagittal radius ($R_S$). Preferably, this radius is approximately 104% to 120% of the first sagittal radius ($R_1$) of the condylar elements 20, 22 of femoral component 12.

The curvature of the condyles 42, 44 of the tibial bearing member 34 lying in the coronal plane and extending in the medial-lateral direction is defined by a coronal radius ($R_c$). The coronal radius of the condyles 42, 44 of the tibial bearing member preferably is approximately 120% to 152% of the coronal radius ($R_3$) of the condyles 20, 22 of the femoral component 12.

Figure 10:
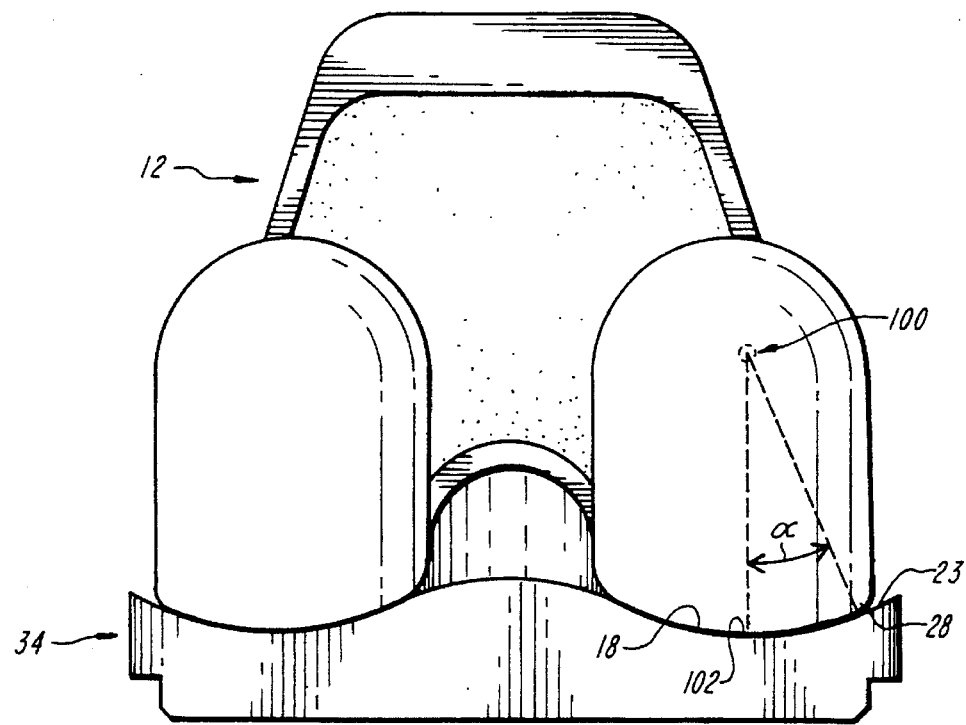
FIG. 10 is a posterior view of a femoral component constructed according to the present invention.

The arc angle of the femoral component 12 of the prostheses of the present invention is dependent on the size of the femoral component. The arc angle ($\alpha$), as illustrated in FIG. 10, is the angle between a line drawn from the arc center 100 to the lowest point 102 on the articulation surface 18 and a line drawn between the arc center 100 and the lateral edge 28 of the articulation surface 23. The arc angle is directly proportional to the amount of varus-valgus lift that is allowable without incurring edge loading. Further, the arc angle is significant because it accommodates the effects of size and shape of condyles, allowing the condyles of the femoral and tibial components to achieve a suitable fit despite identically "matching" sizes not being used.

The arc angle is size dependent since it is largely a function of the width of the femoral component 12 and the medial-lateral dimension. Table 2 illustrates representative arc angles for femoral components of varying sizes.

TABLE 2

| Femoral Component Size | Largest A–P Dimension | Largest M–L Dimension | Arc Angle |
| --- | --- | --- | --- |
| 2 | 56 mm | 60 mm | 21° |
| 3 | 61 mm | 66 mm | 31° |
| 4 | 65 mm | 71 mm | 40° |
| 5 | 69 mm | 73 mm | 44° |
| 6 | 74 mm | 78 mm | 45° |

The knee joint prosthesis 10 of the present invention provides many advantages. As noted above, the contact area between the femoral component 12 and the tibial bearing member 34 is maximized and contact stress is reduced. Another advantage, however, is that the femoral component of the knee joint prosthesis of this invention can be matched, during surgical implantation procedures, to a tibial bearing member that is of a corresponding size or one that is one size unit larger or smaller. This enables a surgeon to implant an artificial joint to accommodate anatomical needs of a patient. Despite such size mismatching, the knee prostheses of the invention still possess superior contact area and minimized contact stress.

FIGS. 6A and 7A illustrate a known, prior art knee prosthesis in perfect alignment condition (FIG. 6A) and when subjected to malalignment due to 3° varus-valgus lift (FIG. 7A). As illustrated, the lateral condyle 20 of the femoral component 12 separates from the lateral condylar element 42 of the tibial bearing member 34. As a result, the interface of the lateral femoral condyle 20 and the lateral tibial condylar element 42 is subjected to edge loading. By comparison, 3° varus-valgus malalignment of the knee prosthesis of the present invention, shown in FIG. 7B, maintains good contact between the femoral component and tibial bearing member articulation surfaces 18, 40 without edge loading.

Figure 8:
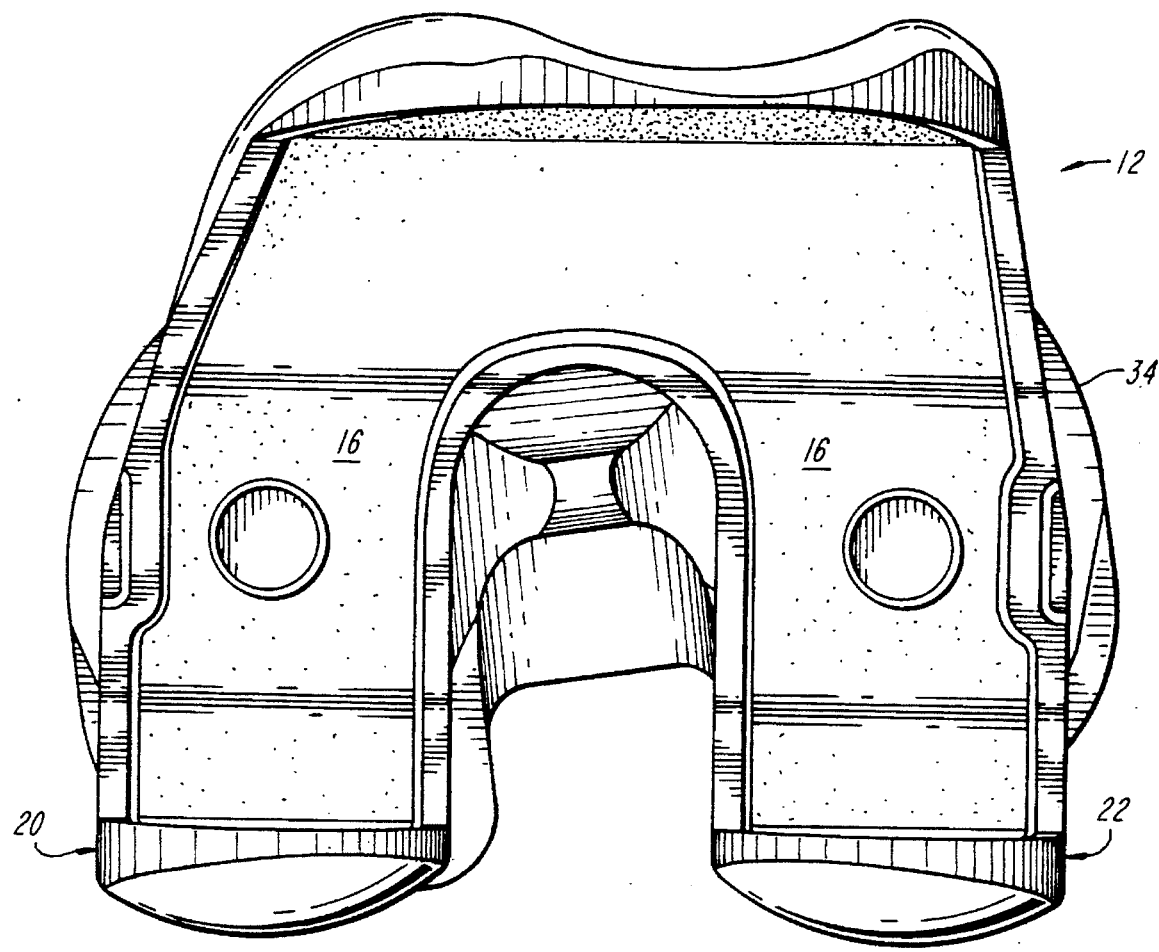
FIG. 8 is a top view of a femoral component of the present invention mounted adjacent to a tibial bearing member, in a malalignment condition having 8° internal-external rotation.

FIG. 8 illustrates a femoral component 12 and a tibial bearing member 34 of the present invention mounted together and subjected to a malalignment condition of 8° internal/external rotation. Despite this malaligmnent, little or no edge loading occurs and good contact is maintained between the articulation surfaces of femoral component 12 and tibial bearing member 34.

Figure 9:
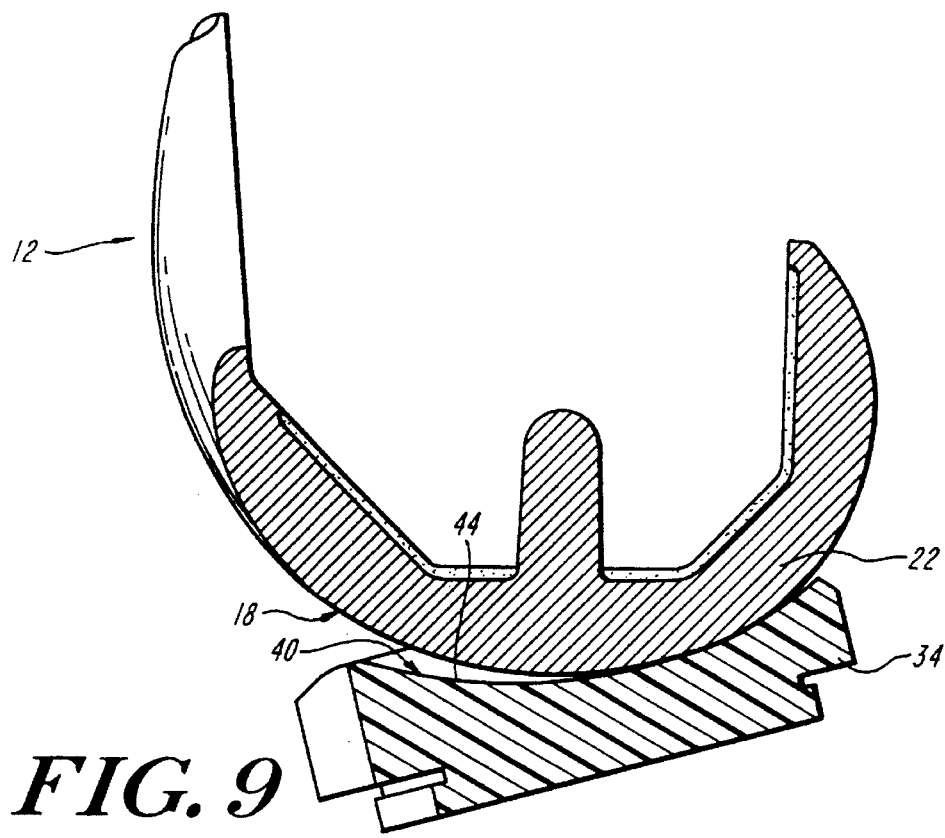
FIG. 9 is a side view (from the medial side) of the femoral component of the present invention mounted adjacent to a tibial bearing member at 15° flexion.

FIG. 9 illustrates the femoral component 12 of the present invention mounted adjacent the tibial bearing member 34 of the present invention during 15° flexion of the knee joint. As illustrated, good contact is maintained between the articulation surfaces of the femoral component 12 and the tibial bearing member 34 during such flexion.

Figure 11:
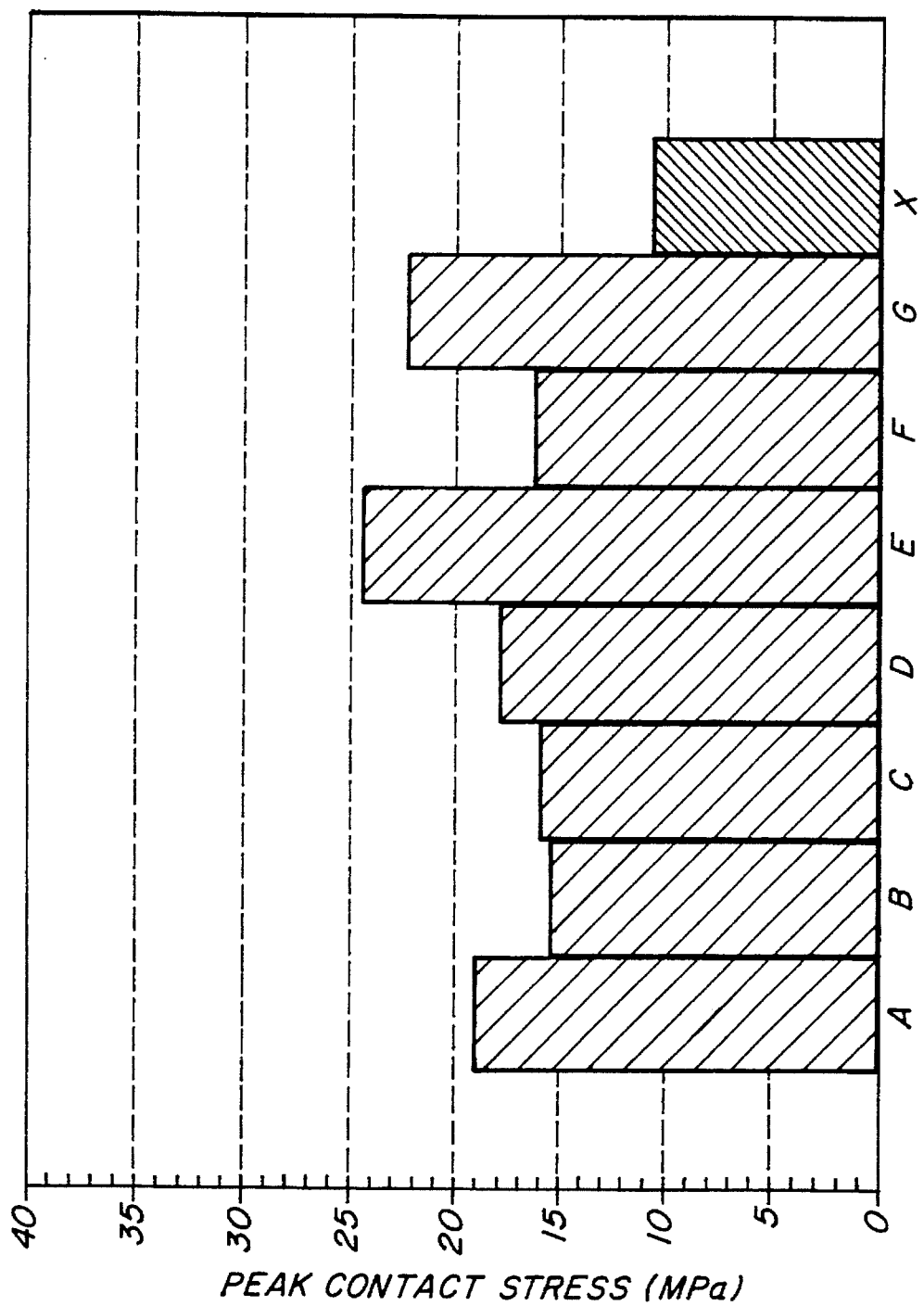
FIG. 11 is a bar graph illustrating the contact stresses that result during the engagement of a prosthetic femoral component with a tibial bearing member, in perfect alignment, for the artificial knee joint of the present invention and various prior art artificial knee joint designs.

FIG. 11 illustrates observed values of contact stress between the articulation surfaces of a femoral component and a tibial bearing member for a variety of prior art knee prostheses (samples A through G), including the knee prosthesis of the present invention (sample X). To generate the data shown in FIG. 11, contact stress was evaluated for a knee prosthesis in an alignment condition of 15° flexion, 3° varus-valgus lift, and 0° internal-external rotation when subjected to a load of about 2060 N, approximately three times average body weight.

The experimental protocol required that the femoral components be cemented to an appropriate holding block by forcing the femoral component onto the block (which bears a cement) until the femoral component can move no further. Tibial trays are then cemented onto tibial holding blocks. A rotary indexing table is then fastened onto a x-y plate which is bolted to an Instron 1123 tensile compressive mechanical testing machine. The rotary indexing table is leveled and shimmed, if necessary. This apparatus is attached to the Instron 1123 in an orientation rotated approximately 45° clockwise from the anterior forward position.

The femoral test block is then fastened to a femoral block holding bracket and this assembly is screwed into the load cell of the Instron 1123. Next, the tibial holding block is bolted onto the base plate of the rotary indexing table. The femoral assembly (without the femoral components attached) is placed against the tibial holding block. The femoral assembly should be adjusted such that the tibial holding block is perpendicular to the femoral block holder. (The rotary dial is not used in the alignment process.)

Prior to testing, the tibial inserts are soaked in a water bath (37° C.±1° C.) for about 18–24 hours. The tests are conducted within an environmental chamber which is at a temperature of 37° C.±1° C. and at 80–90% relative humidity. When the chamber reaches the desired temperature and humidity levels, the tibial insert is removed from the bath and inserted into the tibial holding fixture. During testing the femoral component can be set at a desired flexion angle.

At the outset of testing a crosshead speed of 2 mm/minute, with a 500 kg full scale setting on the Instron chart recorder, is set. An interpositional film having an electrode sensor grid, such as TEKSCAN, available from Tekscan, Inc. of Boston, Mass. is then placed between the femoral and tibial components. The real time screen is opened and the force calibration is performed. The sensor is placed between the femoral component and the tibial insert. Loading is ideally located at the center of the sensor grid. The TEKSCAN technology then prompts the user to enter the load value applied. Next, the femoral is loaded onto the tibil insert (and the TEKSCAN sensors). The load is allowed to increase until the appropriate level is reached. At that instant, the "stop" button on the Instron displacement controller and the "Enter" key on the PC keyboard are depressed simultaneously. The contact stress and contact area are recorded and the load is then removed.

As illustrated, the prosthesis of the present invention exhibited peak contact stress well below that of prior art knee prostheses. The knee prosthesis of the present invention displayed contact stress of approximately 11 MPa, while contact stress for prior art knee prostheses ranged from 16 to 24 MPa.

Figure 12:
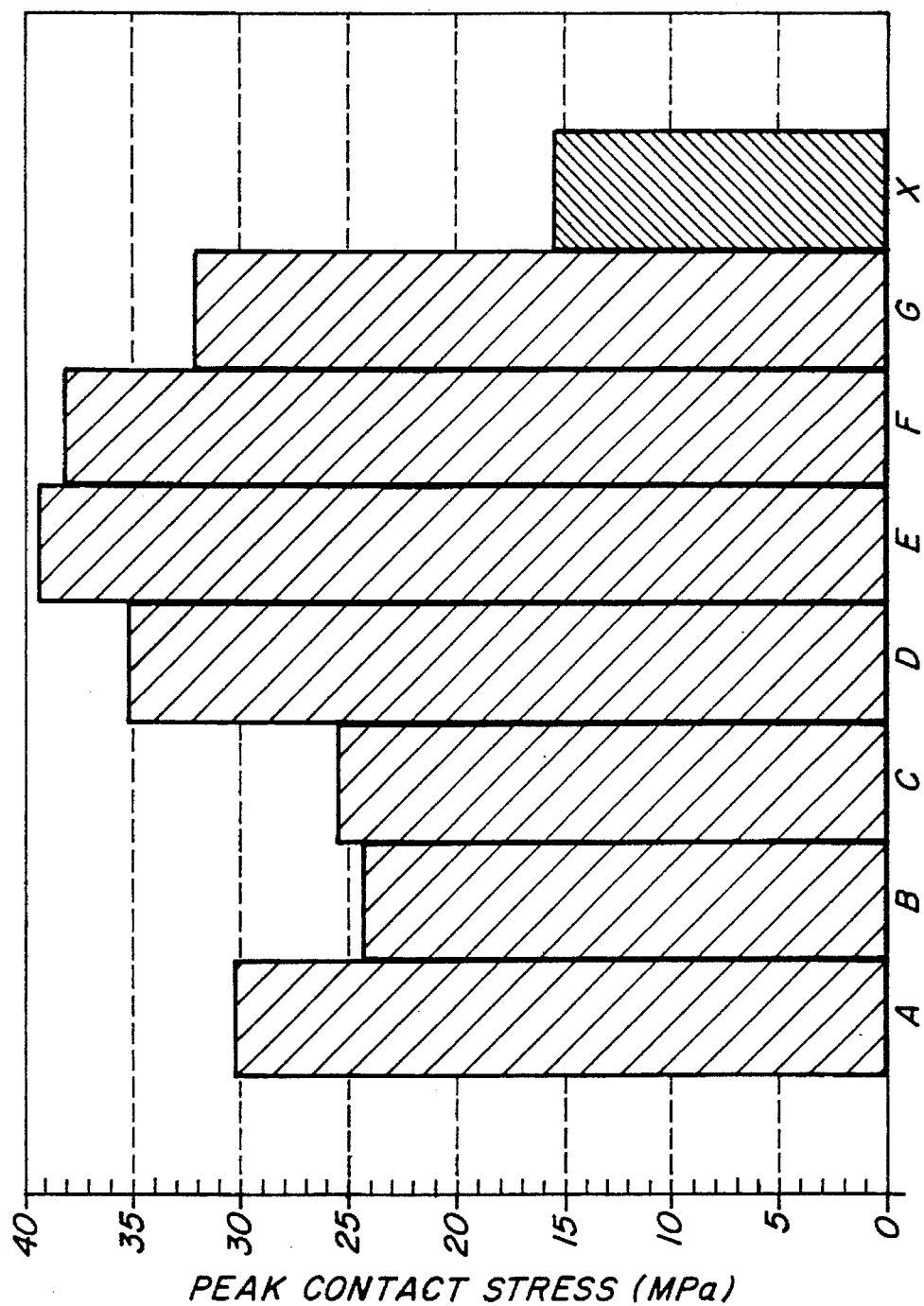
FIG. 12 is a bar graph illustrating the contact stresses that result during the engagement of a prosthetic femoral component with a tibial bearing member in malalignment conditions for the artificial knee joint of the present compared to various prior art artificial knee joint designs.

FIG. 12 shows the results of an evaluation of the peak contact stress, using the same test method used to generate the data of FIG. 11, except that the knee prostheses were in a malalignment condition of 15° flexion, 3° varus-valgus lift, and 0° internal-external rotation. The present knee prosthesis (sample X) demonstrated contact stress of approximately 16 MPa while contact stress developed using prior art knee prosthesis ranged from approximately 24 MPa to 30 MPa, as shown in FIG. 12.

Figure 13:
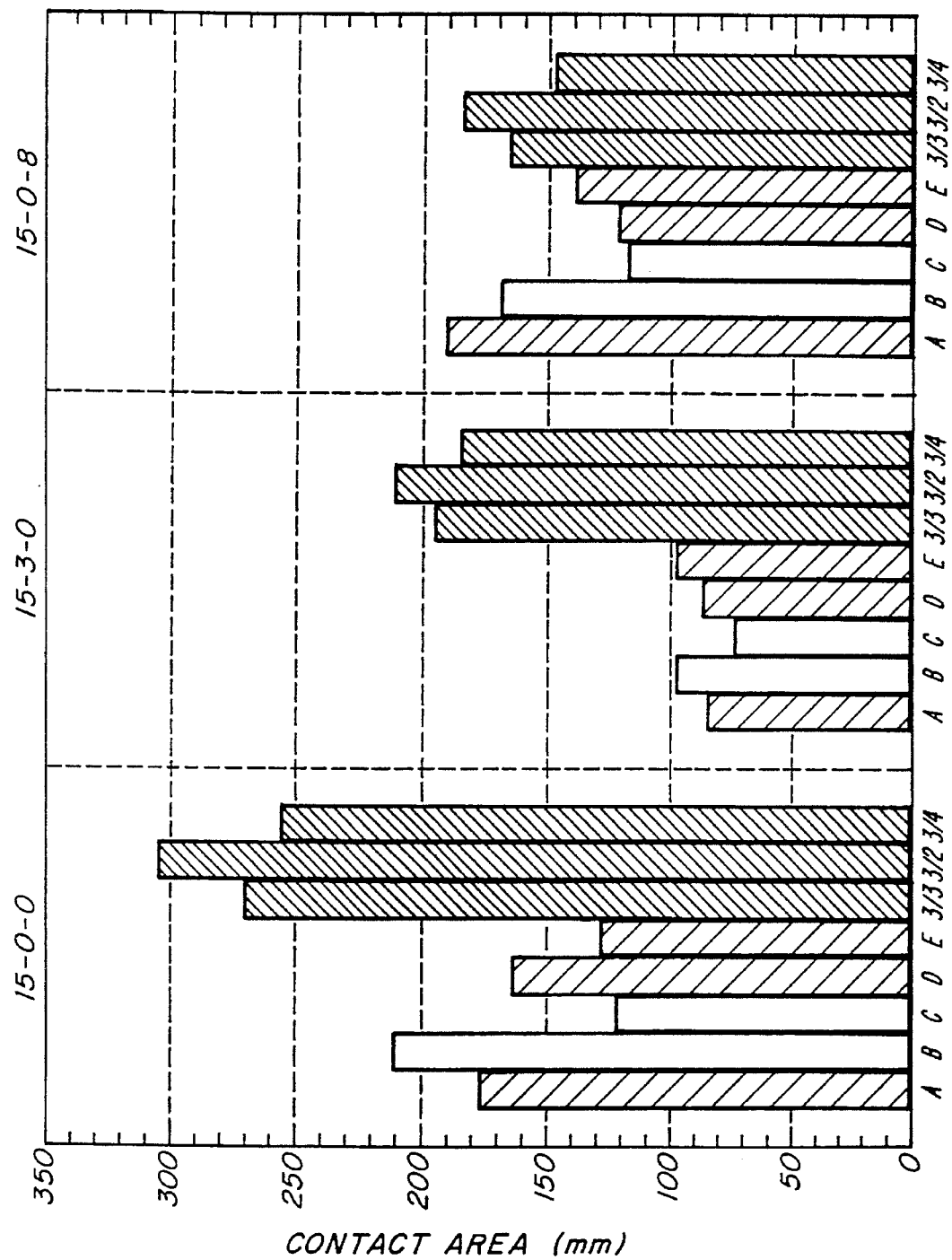
FIG. 13 is a bar graph illustrating the contact area of the engagement between prosthetic femoral components and prosthetic tibial bearing members of artificial knee joints constructed according to the present invention as compared to various prior art artificial knee joint constructions in different conditions of alignment.

FIG. 13 illustrates data obtained while comparing the contact area between femoral and tibial components of various knee prostheses in three different alignment conditions. The alignment conditions evaluated were 15° flexion, 0° varus-valgus lift, and 0° internal/external rotation (15-0-0); 15° flexion, 3° varus-valgus lift, and 0° internal/external rotation (15-3-0); and 15° flexion, 0° varus-valgus lift, and 8° internal/external rotation (15-0-8). The data shown in FIG. 13 was also generated using the procedure described above as the TEKSCAN technology provides both contact area and contact stress in defined areas of a knee joint prosthesis.

Prior art knee joint samples are designated as samples A through E in FIG. 13. Samples of the present invention are designated as samples 3/2, 3/3, and 3/4. In designating samples of the present invention, the first numeral refers to femoral component size, as defined in table 1 and 2, while the second numeral refers to tibial bearing member size.

The contact area between femoral and tibial components of various knee prostheses, in the 15-0-0 alignment condition, illustrated in FIG. 13, established that knee joints of the present invention (samples 3/2, 3/3, and 3/4) demonstrated significantly higher contact area than did the prior art knee prostheses evaluated. A knee prosthesis of the present invention, using a size 3 femoral component (61×66 mm) and a size 3 tibial bearing member (47×71 mm) (sample 3/3) demonstrated a contact area of approximately 270 mm$^2$. A size 3 femoral component matched with a size 2 tibial bearing member (43×64 mm) (sample 3/2) achieved contact area of approximately 310 mm$^2$. A size 3 femoral component matched with a size 4 tibial bearing member (51×76 mm$^2$) (sample 3/4) achieved contact area of approximately 355 mm$^2$. By comparison, prior art knee prostheses demonstrated contact areas ranging from approximately 120 to 210 mm$^2$ in the 15-0-0 alignment condition.

FIG. 13 also illustrates that the contact area of three knee prostheses size configurations according to the present invention (3/3, 3/2 and 3/4) achieved contact areas of 190 mm$^2$, 210 mm$^2$, and 170 mm$^2$, respectively, when the knee joint was subjected to a 15-3-0 malalignment condition Other knee prostheses evaluated had contact areas that ranged from approximately 70 to 97 mm$^2$ under the same test conditions.

The three knee prosthesis size configurations of the present invention (3/3, 3/2, and 3/4) also demonstrated relatively high contact area when subjected to a 15-0-8 malalignment condition The knee prostheses of the present invention exhibited contact of 170 mm$^2$ for the ⅗ size configuration, 185 mm$^2$ for the ½ size configuration, and 147 for the ¾ size configuration. The prior art knee prostheses evaluated exhibited contact area ranging from about 119 to 190 mm$^2$ under the same conditions.

The design and geometry of the articulation surfaces of the femoral component and tibial bearing member of the knee prostheses made according to the present invention lends itself to use with a variety of different constructions for a knee joint prostheses. That is, the articulation surface design and geometry described herein may be incorporated to knee joint prostheses such as cruciate retaining knee prostheses, cruciate sacrificing knee prostheses, meniscal bearing prostheses, hinge prostheses, and unicondylar prostheses.

It will be appreciated by those of ordinary skill in art, that the knee prostheses of the invention can be made from a variety of biocompatible materials having high strength, durability and resistance to wear debris. Examples of such materials include metal alloys such as cobalt-chromium alloy, titanium-aluminum-vanadium alloy, stainless steel, ceramics, and other materials that are well known for use in the manufacture of implantable bone prostheses. Typically, the femoral component and tibial plateau are made from metal alloys such as cobalt-chromium alloy while the tibial bearing member is made from polymers such as ultra-high molecular weight polyethylene.

The foregoing description of the invention is presented to indicate the range of constructions to which the invention applies. Variations in the physical architecture and dimensions of the knee prostheses will be apparent to those having ordinary skill in the art based upon the disclosure herein and such variations are considered to be within the scope of the invention in which patent rights are asserted, as set forth in the claims appended hereto.

What is claimed is:

1. A knee prosthesis system, comprising:

at least one femoral component having an inferior surface mountable on a distal end of the femur of a patient and a superior articulation surface including two adjacent, semi-parallel bearing surfaces, each bearing surface being of substantially the same curved, convex shape and size both in the anterior-posterior direction and in the medial-lateral direction, wherein the curvature of each bearing surface lying in the sagittal plane, in contact with a tibial condylar element, and extending in the anterior-posterior direction is defined by at least two semi-parallel radii wherein a first sagittal radius is more anterior than a second sagittal radius, and wherein the curvature of each bearing surface lying in the coronal plane, in contact with a tibial condylar element, and extending in the medial-lateral direction is defined by a coronal radius;

at least one tibial component having a proximal end and a distal end mountable on the tibia of a patient; and at least one tibial bearing member having a distal surface mountable within the proximal end of the tibial component and a proximal articulation surface, the proximal articulation surface including two adjacent tibial condylar elements, each having substantially the same size and shape, that seat the adjacent semi-parallel bearing surfaces of the femoral component, each condylar element being of a curved, concave shape in both the anterior-posterior and medial-lateral directions, the curvature of the tibial condylar elements in the anterior-posterior direction being defined by a single radius that is approximately 104% to 120% of the first sagittal radius, medial-lateral direction being defined by a single radius that is approximately 120% to 152% of the coronal radius.

the prosthesis being characterized by improved contact between the femoral bearing surfaces and the tibial condylar elements throughout the range of motion of a knee joint such that contact stress between the bearing surfaces of the femoral component and the condylar elements of the tibial bearing member, when subject to a load of approximately 2060 N, does not exceed approximately 15 MPa when the prosthesis is in perfect alignment and does not exceed approximately 20 MPa when the prosthesis is subjected to varus-valgus lift and/or internal-external rotation conditions of malalignment.

2. The prosthesis system of claim 1 wherein the first and second sagittal radii increase with increasing sizes of the femoral components within the prosthesis system.

3. The prosthesis system of claim 2 wherein the first sagittal radius in contact with the tibial condylar element during flexion of a knee joint between about 0° and 40°, is in the range of about 1.020 to 1.885 inches.

4. The prosthesis system of claim 2 wherein the second sagittal radius, in contact with the tibial condylar element during flexion of a knee joint greater than about 40°, is in the range of about 0.7 to 1.1 inches.

5. The prosthesis system of claim 1 wherein the coronal radius is independent of the size of the femoral components within the prosthesis system.

6. The prosthesis system of claim 5 wherein the coronal radius is in the ratage of about 0.7 to 1.1 inches.

7. The prosthesis system of claim 1 wherein the contact area between the bearing surfaces of the femoral component and the condylar elements of the tibial bearing member, when the prosthesis is subjected to approximately 15° flexion without malalignment, is greater than 200 mm².

8. The prosthesis system of claim 1 wherein the contact area between the bearing surfaces of the femoral component and the condylar elements of the tibial bearing member, when the prosthesis is subjected to approximately 15° flexion and 3° varus-valgus lift, is greater than 130 mm².

9. The prosthesis system of claim 1 wherein one of the femoral components of the system can be implanted with a tibial bearing member of the system that is of a corresponding size, or a tibial bearing member of the system that is one size unit larger or smaller than a corresponding size, without compromising performance of the prosthesis system.

10. A knee prosthesis system, comprising:

at least one femoral component having an inferior surface mountable on a distal end of the femur of a patient and a superior articulation surface including two adjacent, semi-parallel bearing surfaces, each bearing surface being of a curved, convex shape both in the anterior-posterior direction and in the medial-lateral direction, wherein the curvature of each bearing surface lying in the sagittal plane, in contact with a tibial condylar element, and extending in the anterior-posterior direction is defined by at least two sagittal radii wherein a first sagittal radius, more anterior than a second sagittal radius, is about 1.020 to 1.885 inches, and the second sagittal radius is about 0.7 to 1.1 inches, and wherein the curvature of each bearing surface lying in the coronal plane, in contact with a tibial condylar element, and extending in the medial-lateral direction is defined by a coronal radius of about 0.7 to 1.1 inches;

at least one tibial component having a proximal end and a distal end mountable on the tibia of a patient; and at least one tibial bearing member having a distal surface mountable within the proximal end of the tibial component and a proximal articulation surface, the proximal articulation surface including two adjacent tibial condylar elements that seat the adjacent, semi-parallel bearing surfaces the femoral component each condylar element being of a curved, concave shape in both the anterior-posterior and medial-lateral directions wherein the curvature of the condylar elements in the anterior-posterior direction is defined by a radius that is approximately 104% to 120% of the first sagittal radius and the curvature of the condylar elements in the medial-lateral direction is defined by a radius that is approximately 120% to 152% of the coronal radius of the bearing surfaces of the femoral component:

the prosthesis being characterized by improved contact area and reduced contact stress between the femoral bearing surfaces and the tibial condylar elements throughout the range of motion of a knee joint and in conditions of malalignmnent.

11. A knee prosthesis system, comprising:

at least one femoral component having an inferior surface mountable on a distal end of the femur of a patient and a superior articulation surface including at least one condylar bearing surface being of a curved, convex shape both in the anterior-posterior direction and in the medial-lateral direction, wherein the curvature of the bearing surface lying in the sagittal plane is defined by at least two semi-parallel radii wherein a first sagittal radius is more anterior than a second sagittal radius, and wherein the curvature of the bearing surface lying in the coronal plane is defined by a coronal radius;

at least one tibial component having a proximal end and a distal end mountable on the tibia of a patient; and at least one tibial bearing member having a distal surface matable with the proximal end of the tibial component and a proximal articulation surface, the proximal articulation surface including at least one tibial condylar element that seats the at least one condylar bearing surface of the femoral component, the tibial condylar bearing member being of a curved, concave shape in both the anterior-posterior and medial-lateral directions, the curvature of the tibial condylar element in the anterior-posterior direction being defined by a single radius that is approximately 104% to 120% of the first sagittal radius and in the medial-lateral direction being defined by a single radius that is approximately 120% to 152% of the coronal radius of the bearing surface of the femoral component;

the prosthesis being characterized by improved contact between the femoral bearing surface and the tibial condylar element throughout the range of motion of a knee joint such that the contact stress between the bearing surface of the femoral component and the condylar elements of the tibial bearing member, when subject to a load of approximately 2060N. does not exceed, approximately 15 MPa when the prosthesis is subjected to conditions of malalignment.

* * * * *

UNITED STATES PATENT AND TRADEMARK OFFICE
CERTIFICATE OF CORRECTION

PATENT NO. : 5,609,643
DATED : March 11, 1997
INVENTOR(S) : Dennis P. Colleran et al.

It is certified that error appears in the above-indentified patent and that said Letters Patent is hereby corrected as shown below:

Column 3, line 25, change "104% to 120%" to --120% to 152%--;

Column 3, lines 29-30, change "120% to 152%" --104% to 120%--;

Column 6, line 48, change "104% to 120%" to --120% to 152%--;

Column 6, line 54, change "120% to 152%" --104% to 120%--;

Column 10, line 43, change "104% to 120%" to --120% to 152%--;

Column 10, lines 45-46, change "120% to 152%" --104% to 120%--;

Column 12, line 2, change "104% to 120%" to --120% to 152%--;

Column 12, line 5, change "120% to 152%" --104% to 120%--;

UNITED STATES PATENT AND TRADEMARK OFFICE
CERTIFICATE OF CORRECTION

PATENT NO. : 5,609,643
DATED : March 11, 1997
INVENTOR(S) : Dennis P. Colleran et al.

It is certified that error appears in the above-identified patent and that said Letters Patent is hereby corrected as shown below:

Column 12, line 37, change "104% to 120%" to --120% to 152%--; and

Column 12, lines 40-41, change "120% to 152%" --104% to 120%--.

Signed and Sealed this

Tenth Day of March, 1998

Attest:

BRUCE LEHMAN

*Attesting Officer*     *Commissioner of Patents and Trademarks*